(12) United States Patent
Zhao et al.

(10) Patent No.: US 10,012,576 B2
(45) Date of Patent: Jul. 3, 2018

(54) IN-SITU TESTING EQUIPMENT FOR TESTING MICROMECHANICAL PROPERTIES OF MATERIAL IN MULTI-LOAD AND MULTI-PHYSICAL FIELD COUPLED CONDITION

(71) Applicant: Jilin University, Nanguan Changchun, Jilin (CN)

(72) Inventors: Hongwei Zhao, Jilin (CN); Luquan Ren, Jilin (CN); Jianping Li, Jilin (CN); Hu Huang, Jilin (CN); Panfeng Zhang, Jilin (CN); Xiaoli Hu, Jilin (CN); Hongbing Cheng, Jilin (CN); Daining Fang, Jilin (CN); Zhichao Ma, Jilin (CN); Qingwei Zhuang, Jilin (CN); Jing Gao, Jilin (CN); Xiaolong Dong, Jilin (CN); Kehong Tang, Jilin (CN); Fu Zhang, Jilin (CN); Qing Zou, Jilin (CN); Yuxiang Zhu, Jilin (CN); Jingshi Dong, Jilin (CN); Zunqiang Fan, Jilin (CN); Yong Hu, Jilin (CN); Tao Shang, Jilin (CN)

(73) Assignee: JILIN UNIVERSITY, Changchun, Jilin (CN)

( * ) Notice: Subject to any disclaimer, the term of this patent is extended or adjusted under 35 U.S.C. 154(b) by 153 days.

(21) Appl. No.: 15/024,119

(22) PCT Filed: Mar. 3, 2014

(86) PCT No.: PCT/CN2014/072805
§ 371 (c)(1),
(2) Date: Mar. 23, 2016

(87) PCT Pub. No.: WO2015/043137
PCT Pub. Date: Apr. 2, 2015

(65) Prior Publication Data
US 2016/0216182 A1 Jul. 28, 2016

(30) Foreign Application Priority Data
Sep. 26, 2013 (CN) .......................... 2013 1 0444251

(51) Int. Cl.
*G01N 3/06* (2006.01)
*G01N 3/08* (2006.01)
(Continued)

(52) U.S. Cl.
CPC ................. *G01N 3/06* (2013.01); *G01N 3/04* (2013.01); *G01N 3/08* (2013.01); *G01N 3/20* (2013.01);
(Continued)

(58) Field of Classification Search
CPC .. G01N 3/18; G01N 3/54; G01N 3/06; G01N 3/04; G01N 3/20; G01N 3/22; G01N 3/26; G01N 3/08; G01N 3/32
(Continued)

(56) References Cited

U.S. PATENT DOCUMENTS 2,037,529 A * 4/1936 Mooney ................. G01N 11/14
73/150 R
2,763,149 A * 9/1956 Long ........................ G01N 3/10
374/49

(Continued)

FOREIGN PATENT DOCUMENTS

CN 201392291 Y 1/2010
CN 101680828 A 3/2010
(Continued)

OTHER PUBLICATIONS

International Search Report and Written Opinion of the International Searching Authority for corresponding International Patent Application No. PCT/CN2014/072805 dated Jul. 11, 2014, 17 pages.
(Continued)

*Primary Examiner* — Daniel S Larkin
*Assistant Examiner* — David L Singer
(74) *Attorney, Agent, or Firm* — Merchant & Gould P.C.

(57) ABSTRACT

An in-situ testing equipment for testing micromechanical properties of a material in a multi-load and multi-physical field coupled condition is disclosed. The equipment com-
(Continued)

prises a frame supporting module, a tension/compression-low cycle fatigue module, a torsioning module (21), a three-point bending module (6), an impressing module (33), a thermal field and magnetic field application module (34), an in-situ observation module (32) and a clamp body module (22). The testing equipment is capable of realizing applications of five different types of loads including tension/compression, low cycle fatigue, torsion, bending and impressing, performing an intensive study on micromechanical properties of the material in the multi-load and multi-physical field coupled condition by using built-in electric, thermal and magnetic application modules and the in-situ observation module, and acquiring relations between deformation behavior, mechanism of damage, performance weakening of the material, applied loads and material properties.

12 Claims, 9 Drawing Sheets

(51) Int. Cl.
    *G01N 3/20*     (2006.01)
    *G01N 3/22*     (2006.01)
    *G01N 3/26*     (2006.01)
    *G01N 3/04*     (2006.01)
    *G01N 3/32*     (2006.01)

(52) U.S. Cl.
    CPC ................ *G01N 3/22* (2013.01); *G01N 3/26* (2013.01); *G01N 3/32* (2013.01)

(58) Field of Classification Search
    USPC ....................... 73/602, 856–857; 702/42–43; 374/45–52
    See application file for complete search history.

(56) References Cited

U.S. PATENT DOCUMENTS

| | | | | |
|---|---|---|---|---|
| 3,813,919 A | * | 6/1974 | Taniguchi | G01N 3/18 374/50 |
| 5,315,085 A | * | 5/1994 | Ferguson | G01N 3/04 219/396 |
| 5,959,215 A | * | 9/1999 | Ono | G01N 3/36 73/789 |
| 2002/0162400 A1 | * | 11/2002 | Xie | G01N 3/32 73/812 |
| 2007/0169563 A1 | * | 7/2007 | Hohjo | G01N 3/00 73/799 |
| 2008/0223145 A1 | * | 9/2008 | Merendino | G01N 3/38 73/779 |
| 2009/0048788 A1 | * | 2/2009 | Darehbidi | G01N 3/32 702/34 |

FOREIGN PATENT DOCUMENTS

| | | |
|---|---|---|
| CN | 202903617 U | 4/2013 |
| CN | 103499483 A | 1/2014 |
| JP | H03-181838 A | 8/1991 |
| JP | H04-106452 A | 4/1992 |

OTHER PUBLICATIONS

First Chinese Office Action for corresponding Chinese Patent Application No. 201310444251.4, 10 pages (2015).
Second Chinese Office Action for corresponding Chinese Patent Application No. 201310444251.4, 8 pages (2015).
Third Chinese Office Action for corresponding Chinese Patent Application No. 201310444251.4, 8 pages (2015).

* cited by examiner

IN-SITU TESTING EQUIPMENT FOR TESTING MICROMECHANICAL PROPERTIES OF MATERIAL IN MULTI-LOAD AND MULTI-PHYSICAL FIELD COUPLED CONDITION

PRIORITY APPLICATIONS

This application is a U.S. National Stage Filing under 35 U.S.C. 371 from international Application No. PCT/CN2014/072805, filed on 3 Mar. 2014, and published as WO 2015/043137 on 2 Apr. 2015, which claims the benefit of priority to Chinese Application No. 310444251.4, filed on 26 Sep. 2013; which applications and publication are incorporated herein by reference as if reproduced herein and made a part hereof in their entirety, and the benefit of priority of each of which is claimed herein.

TECHNICAL FIELD

Embodiments of the present application relate to field of mechanical test of materials, particularly, to a testing equipment for testing micromechanical properties of materials, and more particularly, to an in-situ testing equipment for testing micromechanical properties of materials in a multi-load and multi-physical field coupled condition. The equipment may apply a single load selected from a group consisted of tension/compression, low cycle fatigue, torsion, bending and impressing, or a combination of two or more loads selected from the group simultaneously to the material to be tested. The equipment may also perform a test on a functional material, such as a ferromagnetic material, a thermomagnetic material, a semiconductive material, etc. in a multi-physical field coupled condition formed by a temperature field, an electric field, a magnetic field and a stress field. With an in-situ observation module, such testing equipment may perform a real time and dynamic observation on the testing process in a complicated stress state and in a multi-physical field. Such equipment may provide effective testing means in researching an inner relation among microstructural profile, transition of property, and micromechanical property of a material, and a law of growth of a crack in a multi-load and multi-physical field coupled condition.

BACKGROUND

Development of human society is based on manufacturing industries, where mechanical properties of materials directly restrain a high-speed development of manufacturing industries, influence developments in fields of aerospace, national defense engineering, industry and agriculture, etc., and influence developments of modern science and technology. Mechanical properties of materials under actual load such as stretching, bending, and fatigue etc. are directly related to safety of industry and agriculture, safety of military equipments and safety of human lives and properties. With rapid development of micro-electromechanical systems (MEMS) and micro-imaging device in recent years, it has been found that changes in microstructure of a material may directly influence its macromechanical properties, thus it is very important to start a study in testing technologies of mechanical properties of materials based on changes microstructures.

Traditional testing technologies on conventional tension, bending, torsion and fatigue tests have been well developed, and can substantially meet the requirement on testing macromechanical properties such as strength and fatigue property. However, such tests are usually offsite tests, which cannot provide a real-time dynamic observation of microstructural profiles of a test piece during the tests. Thus, the inner mechanism of microstructural changes and macromechanical properties of a material cannot be effectively combined to characterize the performance of the material. Specifically, in the condition of an actual practice, the material and a product made of the material are usually under action of more than one load, such as a combination of tension and bending, a combination of bending and shear, a combination of tension and torsion, or the like, in which multiple loads exist at the same time. Mechanical property test in a single load manner cannot accurately reflect the loads applied on material and component in an actual situation, that is, no accurate evaluation can be made on mechanical properties of a material under action of complex load. For example, in consideration of experimental study, a material under action of a tension stress will break at a critical bending stress that is much smaller than its bending strength; and a material under action of a bending stress will break at a critical tension stress that is much smaller than its tensile strength. In current studies, a main way of applying a complex-load mode is accomplished by an irregular clamping device orientated at an angle to an axis of tension/compression of a test piece. Axial loading forces output from a driving source are applied along different axes or at different heights to provide an asymmetrical clamping, such that complex load, such as a combination of tension and bending, or a combination of compression and shear, occurs inside the material. Another way of applying complex load is accomplished by utilizing a complicated and expensive multifunctional material testing machine. However, such a testing machine can only apply certain type of complex load, two or more loads cannot be separately or successively applied, such that no accurate evaluation can be made on mechanical properties of a material and its product and inner mechanism of deformation and damage under the action of complex load, and thus popularization and application of material testing machine are significantly restrained.

With innovations in material science, manufacturing technology, various novel functional material are developed, performances of conventional materials have been improved and application ranges of such materials are extended, thus people have set higher demands on material properties and testing. Before the 1980's, a material testing machine is merely applied in a few fields, such as metal materials, etc. Today, application range of a material testing machine is not limited to metal materials, but has been widely used in all industries. Particularly, with wide use of novel ferroelectric/ferromagnetic, thermomagnetic and semiconductor materials, mechanical properties of material in a multi-physical field, such as a force-electric-thermal-magnetic field, would be more important. Existing commercial testing machine can seldom fulfill the requirements of simulation and testing of properties of a material in the above-described multi-physical field. Thus, it is a trend to develop novel testing machine that can test properties of a material in a multi-physical field.

DISCLOSURE OF THE INVENTION

An object of the application is to provide an in-situ testing equipment for testing micromechanical properties of a material in a multi-load and multi-physical field coupled condition, so as to solve shortcomings of existing testing equipments that can only apply a single load and cannot take a coupling effect of a stress field and externally applied physical fields such as temperature field and magnetic field, and cannot perform an in-situ test. An embodiment of the invention may apply five different types of loads, i.e., tension/compression, low cycle fatigue, torsion, bending, and impressing, and external temperature field, electric field and magnetic field can also be applied, so the testing equipment according to the embodiment of the invention can study micromechanical properties of a material in a "mechanical-electric-thermal-magnetic" multi-load and multi-physical field coupled condition. The five types of loads in a multi-load module can be applied separately, or two or more types of the loads may be combined and applied at the same time (except for a combination of bending and impressing, which cannot coexist). A bending module, an impressing module and a thermal field and magnetic field application module in the testing equipment are interchangeable, such that space required for arranging the modules are saved, and range of test can be enlarged as much as possible. At the same time, the application takes the relation among microstructural change, transition of performance and macromechanical properties of a material into account. An in-situ observation module is integrated, and with a 3D micro-imaging assembly having a large depth of field, an ultrasonic inspection assembly and a Raman spectrometer that are provided in the in-situ observation module, the equipment can perform a real-time dynamically observation during the test in the multi-load and multi-physical field coupled condition. Such equipment may provide an effective testing means in researching mechanical properties, microstructural profile of a material and development of a crack in the multi-load and multi-physical field coupled condition. This application starts from a multi-load mode in an actual condition and theories and methods of testing mechanical properties of material in a mechanical-electric-thermal-magnetic coupled field, and provides an in-situ testing equipment for testing mechanical properties of a material in a "tension/compression-low cycle fatigue-torsion-bending-impressing" multi-load and "mechanical-electric-thermal-magnetic" multi-physical field coupled condition, to fulfill actual requirement in material testing. The testing equipment according to an embodiment of the invention may provide new methods for structural designs of various metal materials, semiconductive materials and functional materials, manufacturing, life prediction and reliability assessment. This study is very important in science and may provide significant benefits in society and economics.

The above object is achieved by the following technical solutions:

An in-situ testing equipment configured for testing micromechanical properties of a material in a multi-load and multi-physical field coupled condition is provided, which comprises a frame supporting module, a tension/compression-low cycle fatigue module, a torsioning module 21, a three-point bending module 6, an impressing module 33, a thermal field and magnetic field application module 34, an in-situ observation module 32 and a clamp body module 22. The frame supporting module provides a structural support for the whole testing equipment; the tension/compression-low cycle fatigue module is arranged at upper and lower ends of the testing equipment; the torsioning module 21 is directly arranged at a front end of the tension/compression-low cycle fatigue module; the three-point bending module 6, the impressing module 33 and the thermal field and magnetic field application module 34 are disposed on a support post at one side of the whole testing equipment through a common replacing component, and the in-situ observation module is disposed on another support post at the other side of the testing equipment. The clamp body module is connected to a front segment of the torsioning module, so as to clamp a test piece. An overall structure of the testing equipment is configured in a vertically symmetrical arrangement achieved by using four support posts; two identical servo hydraulic cylinders 10 and two torsioning modules 21 are located at upper and the lower ends of the testing equipment respectively and are used to perform a symmetrical tension/compression test and a symmetrical torsion test on the test piece 23 positioned centrally, to ensure that the geometrical center of the test piece 23 is maintained stationary during tension/compression and torsion tests, so as to facilitate an in-situ dynamic observation on material performances including deformation and damage of the material during the test; and the testing equipment is capable of realizing effectively restrain a resonance amplitude of the geometrical center (i.e., the center of the test piece). The testing equipment is capable of realizing of applications of five different types of loads including tension/compression, low cycle fatigue, torsion, bending and impressing, performing an intensive study on micromechanical properties of the material in the multi-load and multi-physical field coupled condition by using built-in electric, thermal and magnetic application modules and the in-situ observation modules, and acquiring relations between deformation behaviors, mechanism of damage, performance weakening of the material, and applied loads and material properties.

The tension/compression-low cycle fatigue module comprises a servo hydraulic cylinder 10 and a connecting assembly such as a hydraulic cylinder fixing sleeve 13; the torsioning module 21 comprises a torsion servo motor 44, a worm gear reducer and a ball spline 47; the three-point bending module 6 comprises a bending servo motor 54, a transmission assembly comprising a ball screw 60 and a lead screw nut 61, a pressing head 64, and first and second guide rail-slider assemblies 71, 72; the impressing module 33 comprises an impression servo motor 75, a leading screw-nut assembly 89, piezoelectric ceramic 93, a flexible hinge 81, a force sensor 84, a capacitive displacement sensor 83, a diamond impressing head 87 and several connecting and supporting components; and the clamp body module 22 comprises a clamp 97, a back plate 98 for the clamp, a body 99 of the clamp, a tension-torsion force sensor 100, a connecting body 101 and a lower connection-expansion sleeve 102.

The in-situ observation module is disposed on the frame supporting module for applying the "mechanical-electric-thermal-magnetic" multi-load and multi-physical field, the in-situ observation module comprises an instrument for testing and representing material properties, the instrument comprises a 3D micro-imaging assembly having a large depth of field and an ultrasonic inspection device, and is capable of dynamically monitoring deformation and damage mechanism of the material, microstructural changes and transition of properties during the entire test in the complex mechanical loads and multi-physical field coupled condition.

The three-point bending module 6, the impressing module 33, the thermal field and magnetic field application module 34 are interchangeably mounted through a stationary support plate 5 used as a common mounting and replacing component, such that space required for arranging the modules are saved, and range of test can be enlarged as much as possible, while ensuring application of the coupled multi-load and multi-physical field; the testing equipment has a simple structure and a compact arrangement. The impressing module 33 is integrated on the frame supporting module through the stationary support plate 5 used as the common mounting and replacing component, such that an impressing test may be performed on the test piece in various states in which stress fields and physical fields are coupled in different ways.

The torsioning module 21 separates a tensioning/compressing movement in an axial direction from a torsioning movement by using a worm gear reducing mechanism and a cooperative ball spline to, such that the tension/compression-low cycle fatigue module and the torsioning module 21 are independent from each other and do not interfere with each other.

In the three-point bending module 6, a first guide rail-slider assembly 71 is mounted under the bending bottom plate 70, such that the three-point bending module above can float above a support plate 74 for the bending bottom plate, and thereby an internal force type three-point bending is realized.

Two opposite supporting heads 65 of the three-point bending module 6 are fixedly connected to a rear seat 66 for the supporting heads and are mounted within sliding bearings 68 through tail rotating shafts 67 located at ends of the supporting heads, so as to ensure that orientations of the two rear supporting heads 65 can adaptively adjusted, and a problem that the test piece 23 cannot contact the two supporting heads 65 simultaneously caused by misalignment during assembling and clamping can be eliminated.

The impressing module 33 is configured for adjusting an initial distance between a probe of the capacitive displacement sensor 83 and a reflective plate 85 through a manual translation platform 95.

The clamp body module 22 comprises an expansion sleeve for mounting and clamping the test piece.

The thermal field and magnetic field application module 34 utilizes a permanent magnet 104 to provide a magnetic field; with an adjusting screw 105, different intensities of the magnetic field may be achieved by adjusting a relative position of a magnetic loop formed by the permanent magnet 104 and a soft iron 106. The structure is compact, and a large range of intensity of magnetic field may be adjusted within a relative small space.

An embodiment of the invention is based on "mechanical-electrical-thermal-magnetic" multi-physical field; a mechanical loading part may apply five different types of loads, i.e., tension/compression, low cycle fatigue, torsion, bending and impressing. An electric field may be applied through electrically energizing the test piece, a magnetic field may be applied through a direct-loop method, and a temperature field may be realized by using a combined manner of cooling through a semiconductor and heating through light radiating. The in-situ testing equipment for testing micromechanical properties of a material in a multi-load and multi-physical field may combine four externally applied fields, to meet the requirement of test in the multi-load and multi-physical field coupled condition. The electric field may be applied through a direct current. During testing, a stable direct voltage may be applied by an external direct current power source through two electrodes, and a stable electric field will be formed inside the conductive test piece. Intensity of the electric field may be adjusted through adjusting the externally applied voltage.

The thermal field and magnetic field application module 34 utilizes a Peltier sheet 107 to cool the test piece, the Peltier sheet 107 is energized with a direct current in a given direction, and the large amount of heat will be absorbed at a cooling side of the Peltier sheet, such that the temperature of the test piece is lowered so as to realize a cooling effect.

The thermal field and magnetic field application module 34 utilizes a light radiation method to heat the test piece; two symmetrical light-emitting bodies 108 emit infrared light, and the light is reflected by two arc-shaped reflective surfaces and focused onto one point at the center of the test piece, which makes a temperature of a region around the point increase rapidly, and after a period of time, internal heat is transmitted to the entire piece, such that a temperature required by the test will be achieved. Specifically, a water cooling system 109 is integrated into the thermal field and magnetic field application module 34, such that the temperature field inside the thermal field and magnetic field application module 34 will not be influenced by external temperature.

Beneficial effects of embodiments of the invention lie in that: an integrated and innovative design on structure is provided, such that the equipment has a compact structure and all kinds of functions, and can applied five different types of loads, i.e., tension/compression, low cycle fatigue, torsion, bending, and impressing, on a test piece, and the five different types of loads may be separately applied, or two or more of the loads may be combined and applied to even more veritably simulate an actual condition in practice. The testing equipment may perform mechanical tests on functional materials, such as ferromagnetic materials, thermo-magnetic materials, semiconductors, etc., in a multi-load mode with externally applied physical fields, and in turn, an effective testing means for testing function parameters of functional materials in a multi-physical field. An in-situ observation module is integrated in the frame supporting module of the testing equipment according to an embodiment of the invention, such that during the test on the test piece, with the 3D micro-imaging assembly having large depth of field, the ultrasonic inspection device and the Raman spectrometer that are integrated in the in-situ observation module, the equipment can perform a n in-situ real-time dynamically observation of the microstructural profile of the test piece and development of cracks, and can provide an effective testing means in researching an inner relation between microstructural profile and macromechanical property of a material. The testing equipment according to an embodiment of the invention may provide new methods for developing various solid materials, structural designs, manufacturing, life prediction and reliability assessment.

BRIEF DESCRIPTION OF THE DRAWINGS

The appended drawings introduced herein as a part of the application are used to provide a better understanding of the embodiments of the invention. Exemplary embodiments and the description, which are used to interpret the application, should not be construed as a limitation of the application.

LIST OF NUMERALS IN THE DRAWINGS

1: air-floating vibration insulation platform:
2: first screw;
3: first resilient washer;
4: support post;
5: stationary support plate;
6: three-point bending module;
7: upper support plate;
8: coupling sleeve;
9: expansion sleeve;
10: servo hydraulic cylinder;
11: second screw;
12: second resilient washer;
13: hydraulic cylinder fixing sleeve;
14: third screws;
15: third resilient washer;
16: fourth screw;
17: fourth resilient washer;
18: spacer;
19: fifth screws;
20: fifth resilient washer;
21: torsioning module;
22: clamp body module;
23: test piece;
24: guiding bar;
25: lower sleeve;
26: upper sleeve;
27: hex nut;
28: stud;
29: adjusting shim;
30: sixth screw;
31: sixth resilient washer;
32: in-situ observation module;
33: impressing module;
34: thermal field and magnetic field application module;
35: worm housing;
36: end cap for the worm;
37: first adjusting shim;
38: first rolling bearing;
39: first sleeve;
40: worm shaft;
41: worm;
42: first key;
43: second sleeve;
44: torsion servo motor;
45: second adjusting shim;
46: second rolling bearing;
47: ball spline;
48: first end cap for worm wheel;
49: second sleeve;
50: worm wheel;
51: fixed end cap;
52: second key;
53: second end cap for worm wheel;
54: bending servo motor;
55: speed reducer;
56: socket head cap screw;
57: motor flange;
58: coupling;
59: first EK support;
60: ball screw;
61: lead screw nut;
62: nut coupling member;
63: bending force sensor;
64: pressing head;
65: supporting head;
66: rear seat of the support head;
67: tail rotating shaft;
68: sliding bearing;
69: back plate;
70: bending bottom plate;
71: first guide rail-slider assembly;
72: second guide rail-slider assembly;
73: second EK support;
74: support plate for bending bottom plate;
75: impression servo motor;
76: flange;
77: first bottom plate;
78: second bottom plate;
79: support for displacement sensor;
80: support for manual translation platform;
81: flexible hinge;
82: adjusting screw;
83: capacitive displacement sensor;
84: force sensor;
85: reflective plate;
86: sleeve for impressing head;
87: diamond impressing head;
88: second EK support;
89: leading screw-nut assembly;
90: seat for leading screw-nut;
91: EF support base;
92: fastening screw;
93: piezoelectric ceramic;
94: pre-pressing pad;
95: manual translation platform;
96: LM guide rail-slider;
97: clamp;
98: back plate for the clamp;
99: body of the clamp;
100; tension-torsion force sensor;
101 connecting body;
102: lower connection-expansion sleeve;
103: lower support plate;
104: permanent magnet;
105: adjusting screw;
106: soft iron;
107: Peltier sheet;
108: light-emitting body;
109: water cooling system

DETAILED DESCRIPTION OF PREFERRED EMBODIMENTS

Details and specific embodiments of the invention will be described in conjunction with the accompanying drawings.

Referring to FIG. 1 to FIG. 11, an in-situ testing equipment according to an embodiment of the invention, which is configured for testing micromechanical properties of material in a multi-load and multi-physical field coupled condition, and comprises a frame supporting module, a tension/ compression-low cycle fatigue module, a torsioning module 21, a three-point bending module 6, an impressing module 33, a thermal field and magnetic field application module 34, an in-situ observation module 32 and a clamp body module. The frame supporting module provides a structure support for the whole testing equipment; the tension/compression-low cycle fatigue module is arranged at upper and lower ends of the testing equipment, the torsioning module 21 is directly arranged at a front end of the tension/compression-low cycle fatigue module; the three-point bending module 6, the impressing module 33 and the thermal field and magnetic field application module 34 are disposed on a support post at one side of the whole testing equipment; and the in-situ observation module is disposed on another support post at the other side of the testing equipment. The clamp body module is connected to a front segment of the torsioning module, and functions to clamp a test piece. Overall structure of the testing equipment is configured in a vertically symmetrical manner through using four support posts. Two identical servo hydraulic cylinders 10 and two torsioning modules 21 are located at the upper and the lower ends of the testing equipment respectively and are used to perform a symmetrical tension/compression test and a symmetrical torsion test on the test piece 23 positioned centrally, so as to ensure that the geometrical center of the test piece 23 is maintained stationary during torsion/compression and torsion test.

The frame supporting module mainly comprises an air-floating vibration insulation platform 1, an upper support plate 7, a lower support plate 103 and the support posts 4. Main body of the whole testing equipment is mounted on the air-floating vibration insulation platform 1, such that influence on testing process caused by external vibration can be effectively avoided. The lower support plate 103 is fixed onto a mounting surface of the air-floating vibration insulation platform 1 through a first screw 2 and a first resilient washer 3, four spatially symmetrical support posts 4 are mounted in corresponding mating holes in the upper and lower support plates 7, 103 and fastened through sixth screws 16 and sixth resilient washers 17.

The tension/compression-low cycle fatigue module mainly comprises a servo hydraulic cylinder 10, and connecting pieces such as a hydraulic cylinder fixing sleeve 13. By means of a mounting flange, the servo hydraulic cylinder 10 and the hydraulic cylinder fixing sleeve 13 mate with each other with a tolerance between an axle of the servo hydraulic cylinder and a hole of the hydraulic cylinder fixing sleeve so as to ensure mounting accuracy, and are fastened by a second screw 11 and a second resilient washer 12. The hydraulic cylinder fixing sleeve 13 is rigidly fixed to the upper and lower support plates 7, 103 through a third screw 14 and a third resilient washer 15. A shim 18 is used to adjust a vertical distance between the upper and lower support plates.

Figure 5:
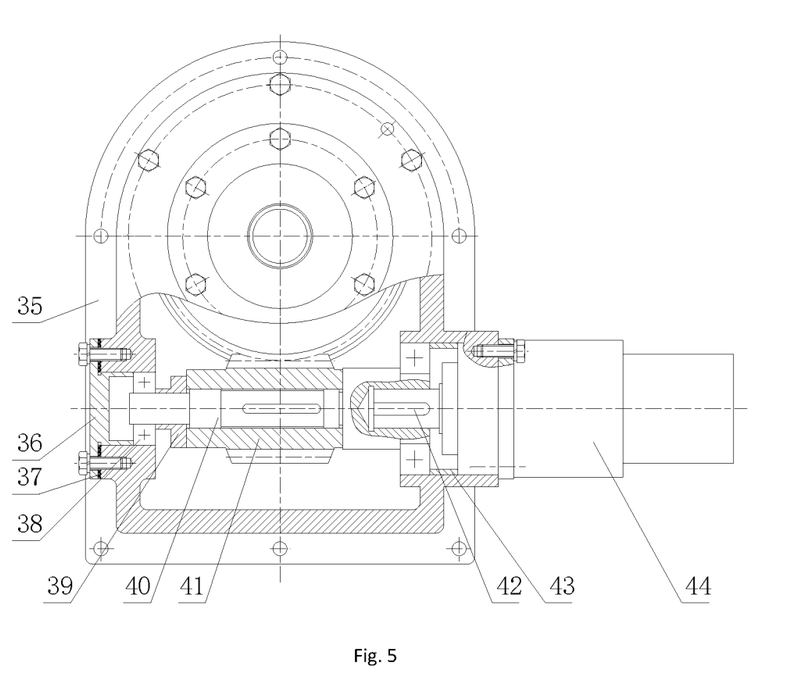
FIG. 5 is a front view of a torsioning module according to an embodiment of the invention.
Figure 6:
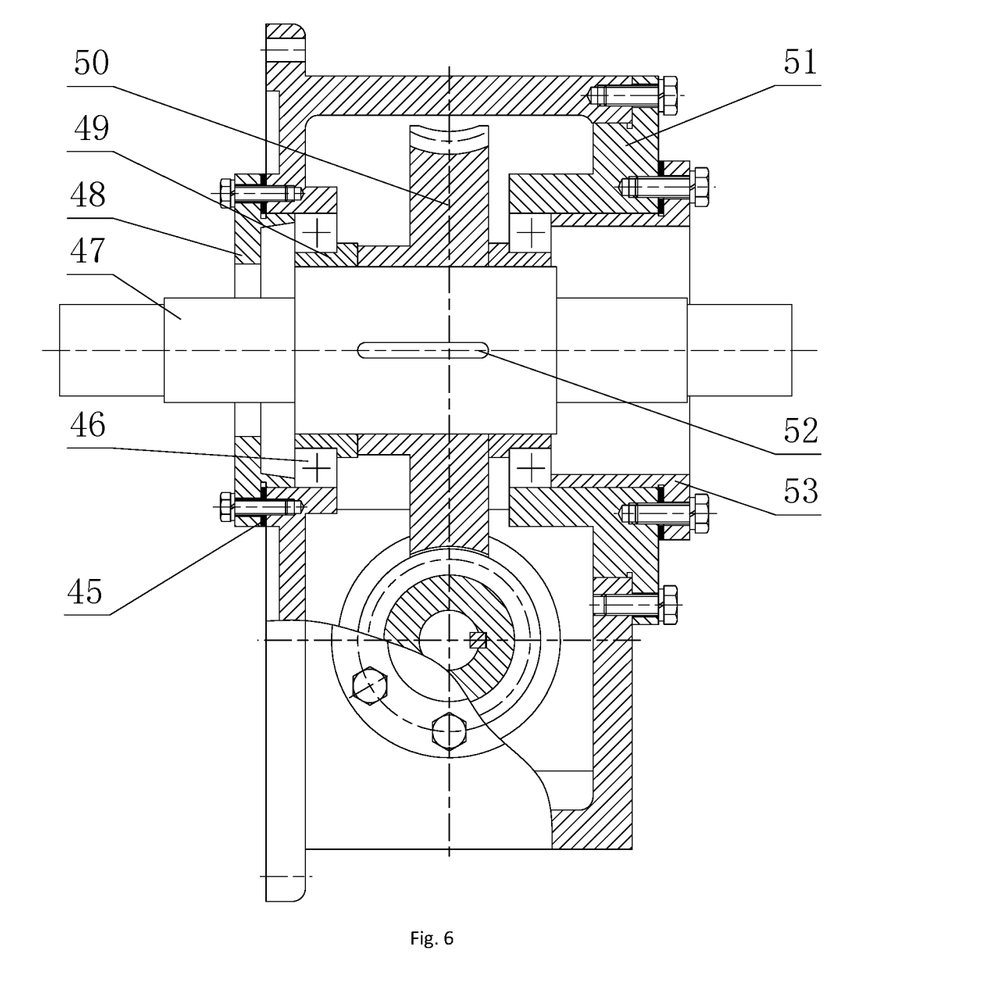
FIG. 6 is a sectional view of the torsioning module according to the embodiment of the invention.

Referring to FIGS. 5 and 6, the torsioning module 21 according to an embodiment of the invention comprises key components such as a torsion servo motor 44, a worm gear reducer and a ball spline 47. An output shaft of the torsion servo motor 44 is connected with a worm shaft 40 through a first key 42. A worm 41 and the worm shaft 40 are connected with each other through a key. A second sleeve 43 is used to maintain an axial position of an outer ring of a rolling bearing. Said worm shaft 40 is supported within a mounting hole of a worm housing 35 through a first rolling bearing 38, and the first sleeve 39 is used to restrict an axial displacement of the worm shaft 41. A position of the outer ring of the first rolling bearing 38 is maintained through a worm end cap 36 and a first adjusting shim 37. An outer spline housing of the ball spline 47 is supported within the mounting hole of the worm housing 35 through a second sleeve 49 and a second rolling bearing 46, and a position of the rolling bearing is maintained through inner flanges of first and second worm wheel end caps 48, 53 and a second adjusting shim 45. A fixed end cap 51 functions as a transition support and a connection. Said worm wheel 50 is connected to the outer spline housing of the ball spline 47 through a second key 52. One end of the ball spline 47 is connected with a rod of the servo hydraulic cylinder 10 through a coupling sleeve 8 and an expansion sleeve 9, the other end thereof is connected to the clamp body module 22 through an expansion sleeve, and the entire torsioning module is fixed to the upper and lower support plate 7, 103 by a fifth screw 19 and a fifth resilient washer 20 via the mounting hole of the worm housing 35.

Figure 1:
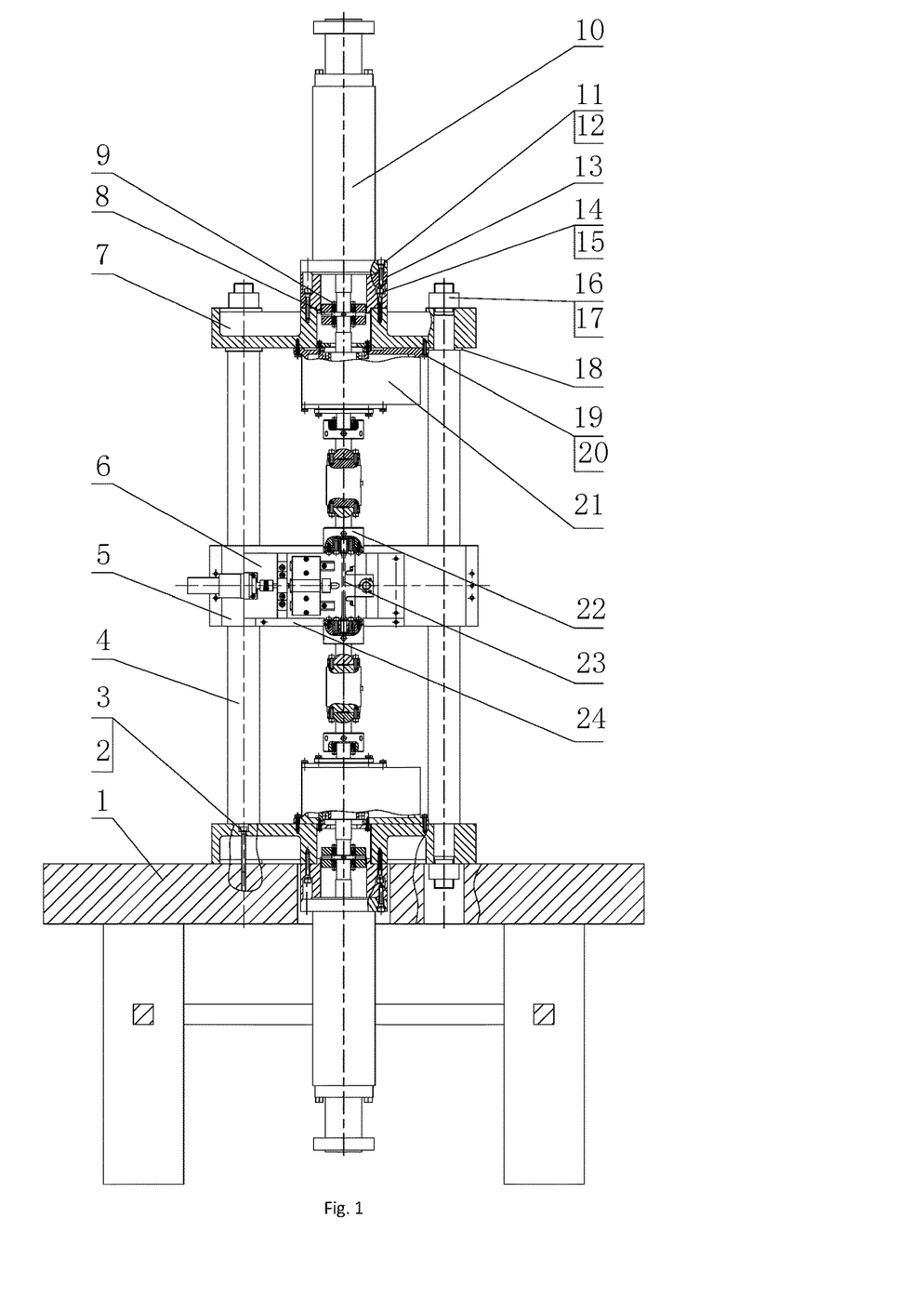
FIG. 1 is an overall front view of an integrated bending module according to an embodiment of the invention.
Figure 2:
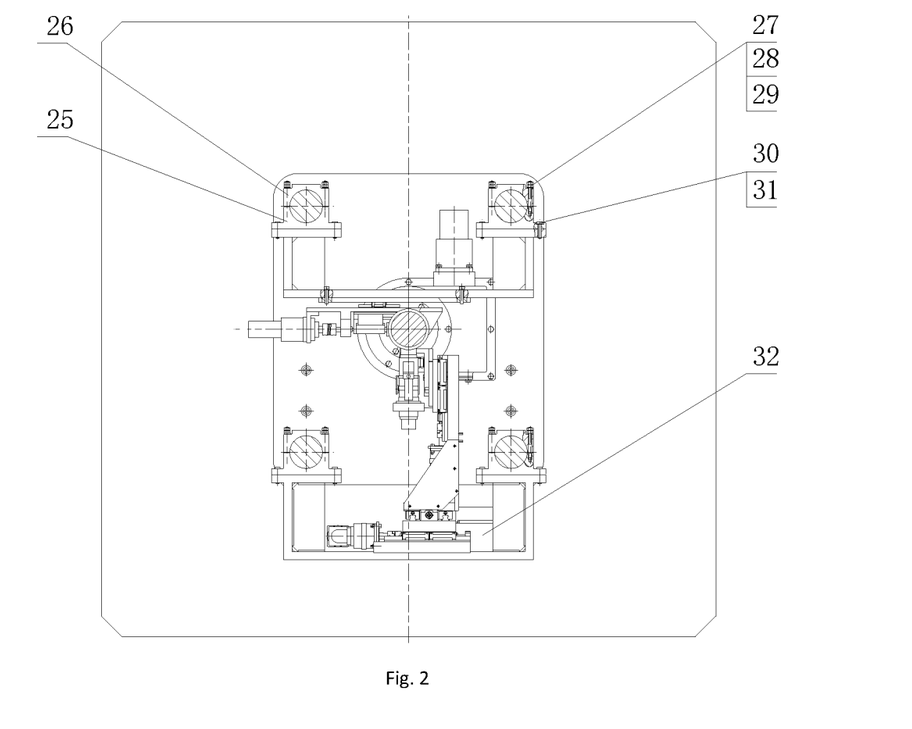
FIG. 2 is an overall top view of the integrated bending module according to the embodiment of the invention.
Figure 7:
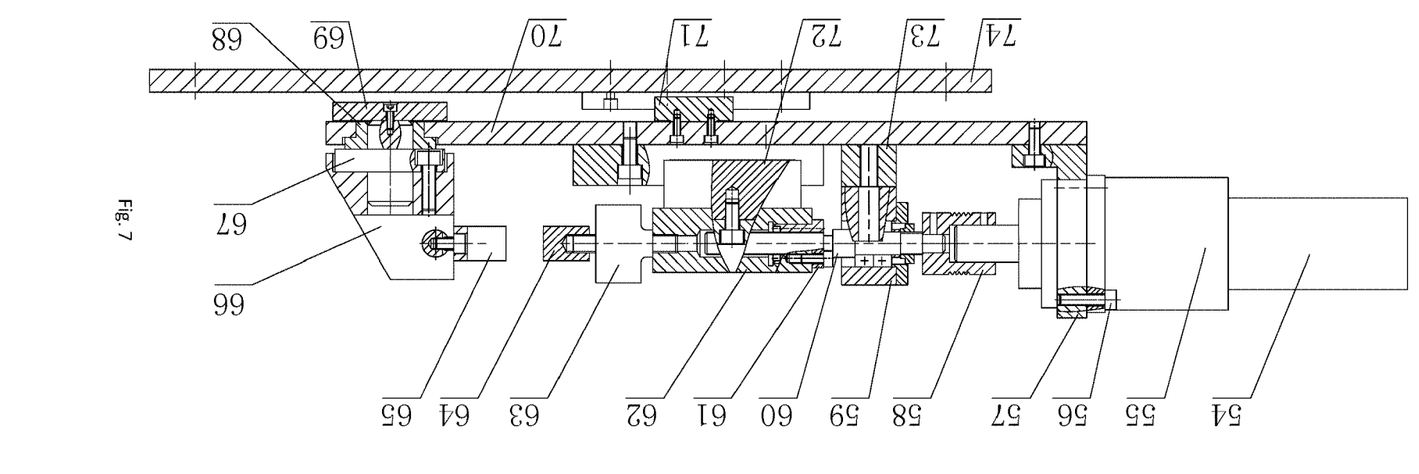
FIG. 7 is a sectional view of a bending module according to an embodiment of the invention.

Referring to FIGS. 1, 2 and 7, the three-point bending module according to an embodiment of the invention mainly comprises a bending servo motor 54, a transmission assembly consisted of a ball screw 60 and a lead screw nut 61, a pressing head 64, and first and second guide rail-slider assemblies 71, 72. The bending servo motor 54 is fixedly connected to a motor flange 57 by a socket head cap screw 56 via a one-stage reducer 55. Power is transmitted to the ball screw 60 via a coupling 58 from an output shaft of the reducer 55, and is converted by the lead screw nut 61 into a linear movement of the pressing head 64 for bending. The ball screw 60 is disposed in a one-end suspended manner by a first EK support 59, and fixed on a bending bottom plate 70 through a first EK support base 73. During a bending test, a bending transverse force is sensed by a bending force sensor 63 which is mounted between a nut coupling member 62 and the pressing head 64, and the nut coupling member 62 is guided by a second guide rail-slider assembly 72 so as to ensure linearity of a displacement of the pressing head 64. Specifically, the three-point bending module utilized in this application is an internal force type three-point bending module, thus the first guide rail-slider assembly 71 is similarly mounted under the bending bottom plate 70, such that the three-point bending module located above may float as a whole relative to a support plate 74 for the bending bottom plate. Correspondingly, in order to ensure an internal force type bending, two supporting heads 65 are disposed at the right side of the pressing head 64, the supporting head 65 is fixedly connected to a supporting head rear seat 66 and mounted within a sliding bearing 68 through a tail rotating shaft 67 located at an end of the supporting head, such that it may ensured that the two supporting heads 65 can be adaptively adjusted by a certain angle during bending, thereby solving the problem that the piece 23 cannot contact both of the supporting heads 65 simultaneously due to non-centering or misalignment during clamping. A back plate 69 is connected to an end of the tail rotating shaft 67, so as to prevent the tail rotating shaft 67 from falling off. Said three-point bending module is mounted through the support plate 74 at the lower end to a common mounting and replacing component, that is, a stationary support plate 5, which is mounted on the a lower sleeve 25 through a sixth screw 30 and a sixth resilient washer 31, and the upper sleeve 25 and a lower sleeve 26 are fixed as a whole on two rear support posts 4 through a hex nut 27, a stud 28 and an adjusting shim 29. A guiding bar 24 mounted on the stationary support plate 5 is used to facilitate mounting and locating respective modules when interchanging the modules.

Figure 3:
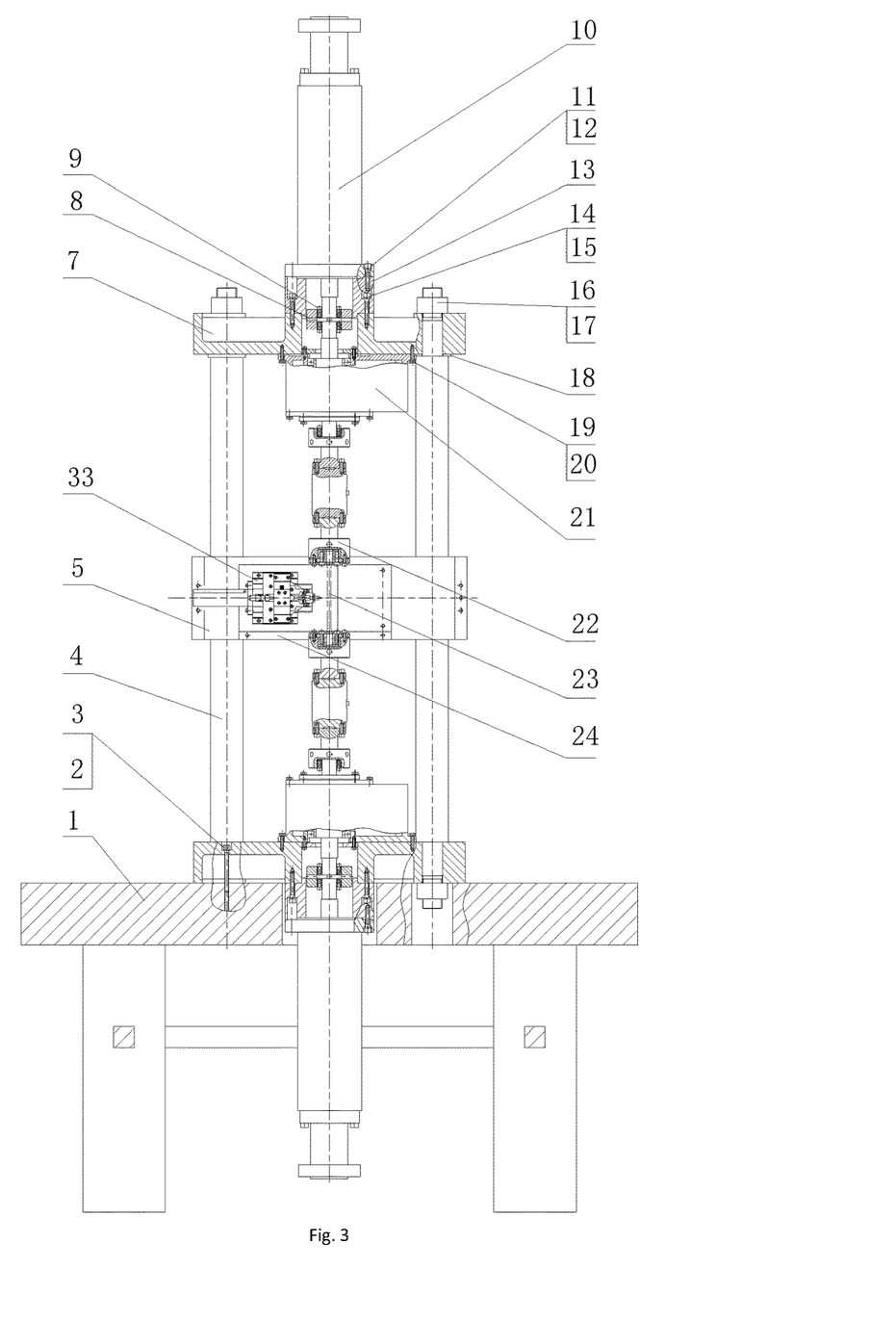
FIG. 3 is an overall front view of an integrated impressing module according to an embodiment of the invention.
Figure 8:
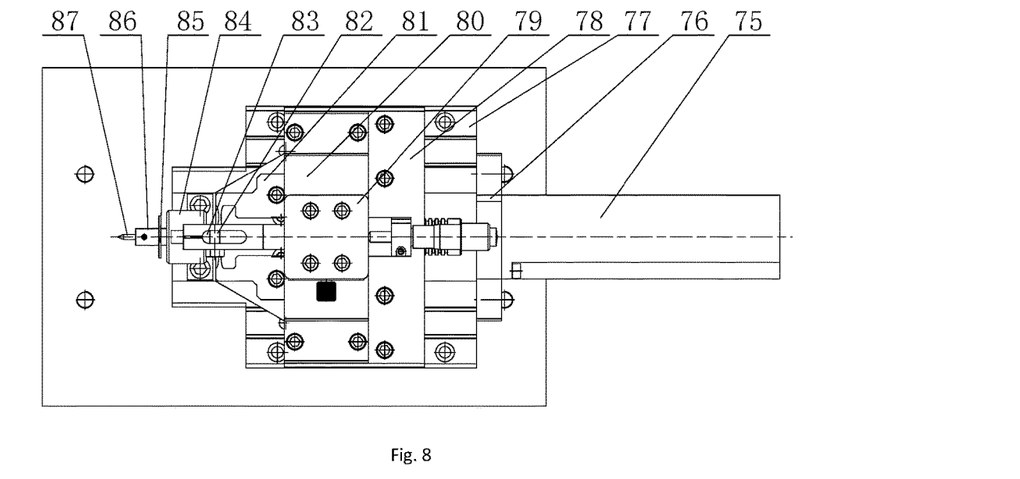
FIG. 8 is a front view of an impressing module according to an embodiment of the invention.
Figure 9:
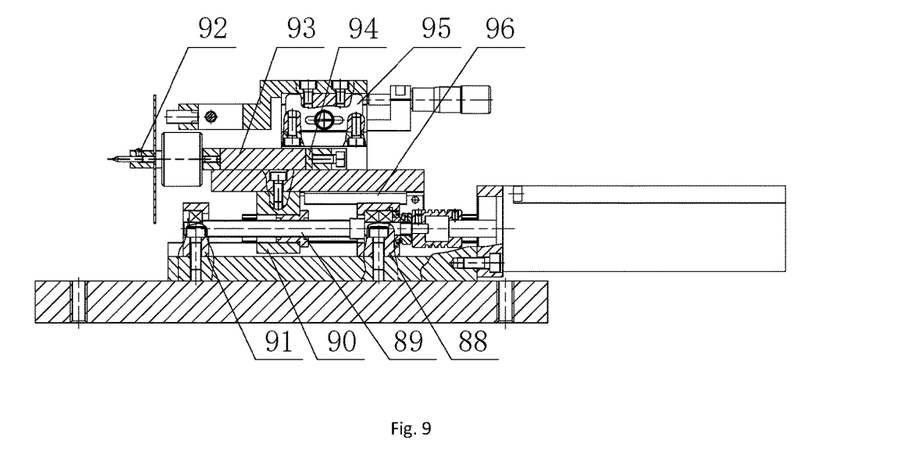
FIG. 9 is a sectional view of the impressing module according to the embodiment of the invention.

Referring to FIGS. 3, 8 and 9, the impressing module according to an embodiment of the invention comprises an impression servo motor 75, a leading screw-nut assembly 89, piezoelectric ceramic 93, a flexible hinge 81, a force sensor 84, a capacitive displacement sensor 83, a diamond impressing head 87 and several connecting and supporting components. The impression servo motor 75 is mounted on a first bottom plate 77 through a flange 76. A second bottom plate 78 is mounted on the first bottom plate 77 through a LM guide rail-slider 96 for direction guidance. A support 79 for the displacement sensor is mounted via a manual translation platform (95) on a support 80 for the manual translation platform. The manual translation platform 95 is used to adjust an initial distance between a probe of the capacitive displacement sensor 83 and a reflective plate 85, and an adjusting screw 82 may be used to fixedly clamp the probe of the displacement sensor. The diamond impressing head 87 is mounted at one end of the force sensor 84 through a sleeve 86 for the impressing head, the other end of the force sensor is connected to the flexible hinge 81 through an external mounting bolt, and a fastening screw 92 may be used to fix the diamond impressing head 87. The piezoelectric ceramic 93 is mounted within a corresponding recess of the flexible hinge 81 and pre-fastened by a pre-pressing pad 94. Power output from the impression servo motor 75 is converted into a linear movement through the leading screw-nut assembly 89, and transmitted by a seat 90 for the leading screw-nut to the flexible hinge 81 so as to be used as a coarse adjusting displacement during impressing. An actual impressing displacement is output by the piezoelectric ceramic. The leading screw-nut assembly 89 in the impressing module is fixed at both ends thereof by a second EK support 88 and an EF support base 91. The whole impressing module is mounted on the common mounting and replacing component, i.e., the stationary support plate 5, through the support plate 74 for the bending bottom plate.

Figure 10:
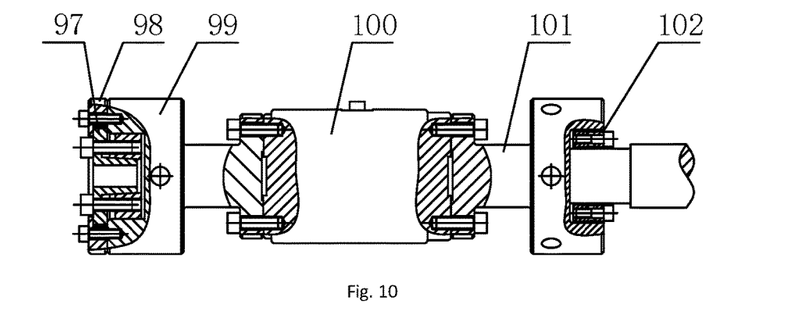
FIG. 10 is a schematic view of a clamp according to an embodiment of the invention.

Referring to FIG. 10, the clamp body module according to an embodiment of the invention mainly comprises a clamp 97, a back plate 98 for the clamp, a body 99 of the clamp, a tension-torsion force sensor 100, a connecting body 101 and a lower connection-expansion sleeve 102. The lower connection-expansion sleeve 102 is connected with an output shaft of the torsioning module, and a tension force may be provided through adjusting a screw on the back plate 98 for the clamp when the test piece is fixedly clamped.

Figure 4:
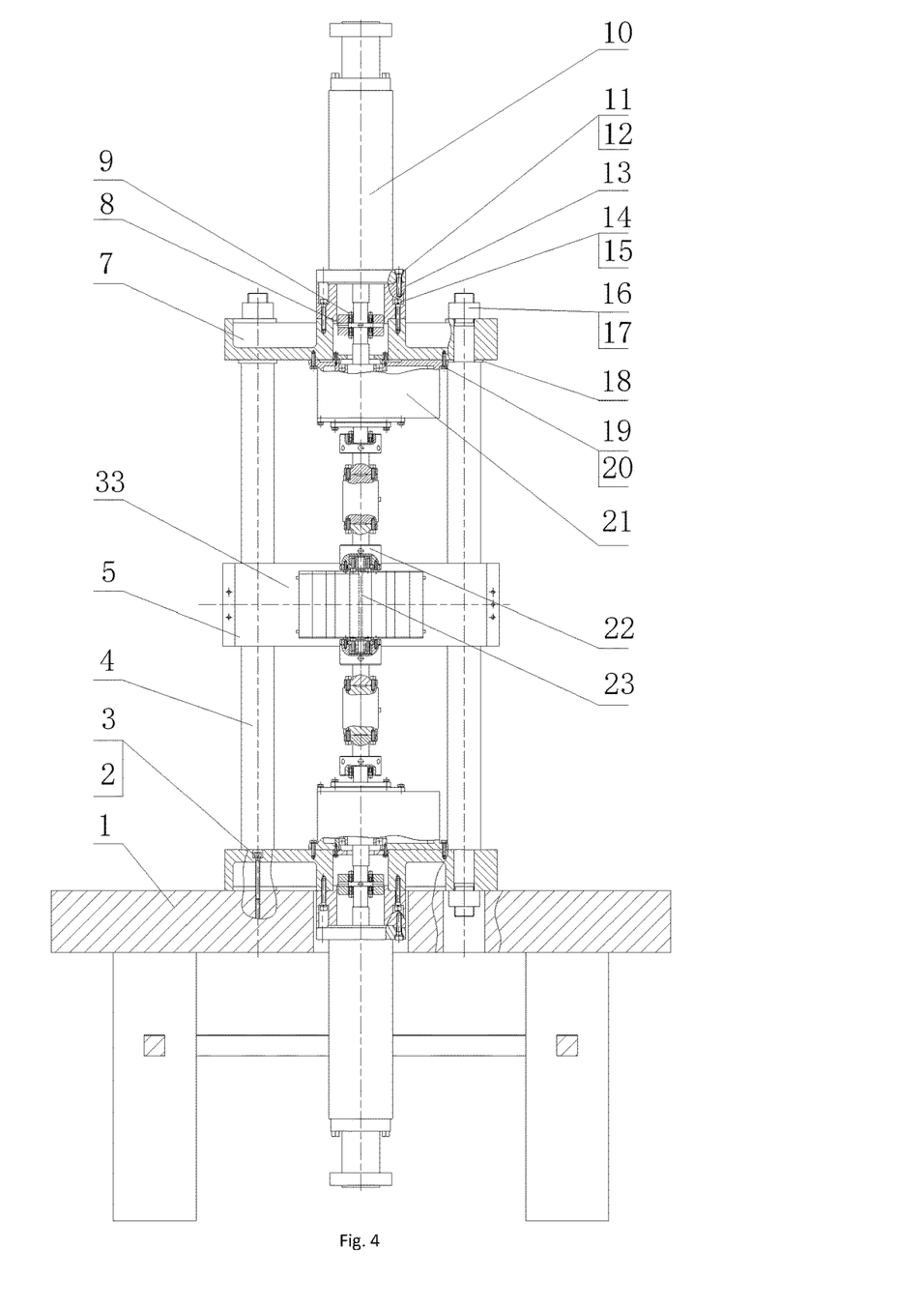
FIG. 4 is an overall schematic view of an integrated thermal field and magnetic field application module according to an embodiment of the invention.
Figure 11:
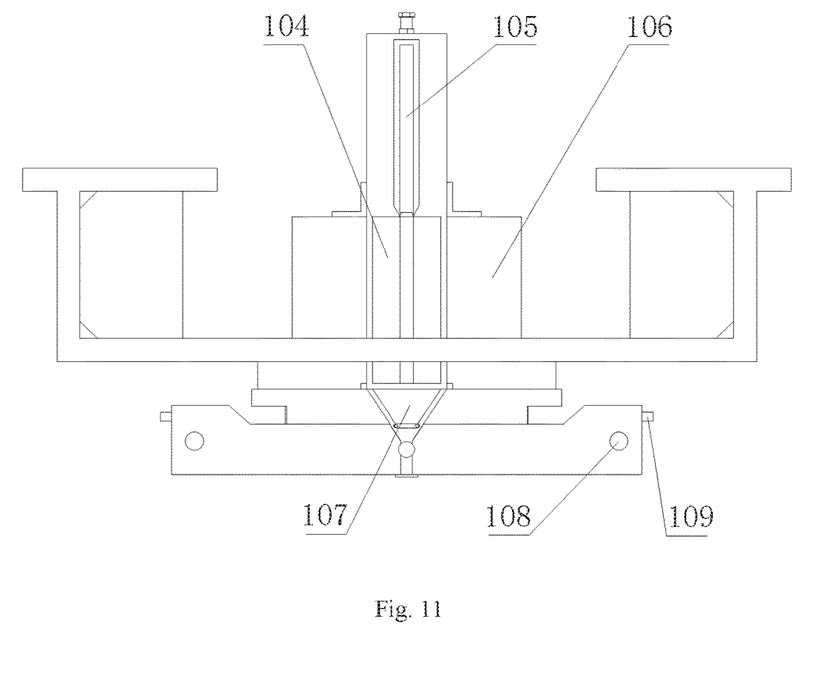
FIG. 11 is a schematic view of a thermal field and magnetic field application module according to an embodiment of the invention.

Referring FIGS. 4 and 11, regarding the application of "mechanical-electrical-thermal-magnetic" physical fields in a coupled way in the embodiment of the invention, a mechanical loading part of the testing equipment may apply five kinds of loads, i.e., tension/compression, low cycle fatigue, torsion, bending and impressing. An electric field may be applied directly through electrically energizing the test piece. During testing, a stable direct voltage may be applied by an external direct current source through two electrodes, and a stable electric field will be formed inside the conductive test piece. Intensity of the electric field may be adjusted through adjusting the externally applied voltage. A thermal field and a magnetic field may be realized by the thermal field and magnetic field application module 34. A magnetic field may be applied by a permanent magnet 104 in the thermal field and magnetic field application module through a direct-loop method; magnetic field of different intensities may be applied through adjusting a relative position of the magnetic loop formed by the permanent magnet 104 and a soft iron 106 by using an adjusting screw 105. The structure is compact, and a large range of intensity of magnetic field may be adjusted within a relative small space. The temperature field may be realized through steps of: cooling the test piece through a semiconductive Peltier sheet 107, the Peltier sheet 107 being energized with a direct current in a given direction and the a large amount of heat being absorbed at a cooling side of the Peltier sheet, such that the temperature of the test piece is lowered so as to realize a cooling effect; and heating the test piece through light radiation. Two symmetrical light-emitting bodies 108 emit infrared light, and the light is reflected by two arc-shaped reflective surfaces and focused onto one point at the center of the test piece, which makes a temperature of a region around the point increase rapidly, and after a period of time, internal heat is transmitted to the entire piece, so that a temperature required by the test will be achieved. Specifically, a water cooling system 109 is integrated in the frame of the thermal field and magnetic field application module 34, such that the table temperature field inside the thermal field and magnetic field application module 34 will not be influenced by external temperature.

The in-situ observation module 32 is also mounted on the common mounting and replacing component, i.e., the stationary support plate 5, and the upper and lower sleeves are mounted on two front side support posts using the same method. The in-situ observation platform has a relative large three-dimensional moving range, and is provided an active vibration insulation device in each of its moving directions. The in-situ observation platform may accurately track an observed point on the test piece, which facilitates tracking the test piece during test.

The whole structure of the equipment of this application utilizes the air-floating vibration insulation platform 1 as a base, such that it can effectively reduce the influence on the testing equipment by external vibration source. The tension/compression-low cycle fatigue module utilizes two high-accuracy hydraulic cylinders 10 as a power source, and a displacement in the tension/compression low cycle fatigue process may be accurately controlled through controlling an amount of oil flowing into the servo hydraulic cylinders 10 and flow direction of oil by a multi-channel servo controller. The torsioning module 21 utilizes a servo motor as a power source, and a torsion angle may be output to a ball spline shaft connected with the rod of the hydraulic cylinder after reduction in speed via a worm gear having a large one-stage reduction gear ratio, driving the rod and the front side clamp body module to rotate as a whole. The three-point bending module 6 is powered by a servo motor, and rotation of the motor is converted into a linear movement of the bending pressing head through a ball screw and nut assembly. The impressing module 33 is powered by a servo motor, and rotation of the motor is converted into a coarse adjusting displacement during an impressing process. An impressing displacement in the impressing process is output by the piezoelectric ceramic via the flexible hinge. A magnetic field is applied by a permanent magnet in the thermal field and magnetic field application module 34 through a direct-loop method. The magnetic fields of different intensities may be loaded through adjusting a relative position of the magnetic loop formed by the permanent magnet 104 and the soft iron 106 by using an adjusting screw 105. The structure is compact, and a large range of intensity of magnetic field may be adjusted within a relative small space. The temperature field may be realized through steps of: cooling the test piece through a semiconductive Peltier sheet 107, the Peltier sheet 107 being energized with a direct current in a given direction and the a large amount of heat being absorbed at a cooling side of the Peltier sheet, such that the temperature of the test piece is lowered so as to realize a cooling effect; and heating the test piece through light radiation. Two symmetrical light-emitting bodies 108 are used to emit infrared light, and the light is reflected by two arc-shaped reflective surfaces and focused onto one point at the center of the test piece to make a temperature of a region around the point increase rapidly, and after a period of time, internal heat is transmitted to the entire piece, so that a temperature required by the test will be achieved. Specifically, a water cooling system 109 is integrated in the frame of the thermal field and magnetic field application module 34, such that the temperature field inside the thermal field and magnetic field application module 34 will not be influenced by external temperature. The application of the electric field is achieved by applying a stable direct voltage on the test piece by an external direct current source via two electrodes, and a stable electric field will be formed inside the conductive test piece. Intensity of the electric field may be adjusted through adjusting the externally applied voltage. Said in-situ observation module 32 may formed as an integrated module, which will not be repeated herein.

During a specific test, firstly a type of load needs to be applied and a type of field to be applied should be determined before the test, then a corresponding impressing module, a three-point bending module or a thermal field and magnetic field application module is mounted via the common mounting and replacing component, i.e., the stationary support plate 5. The servo hydraulic cylinder 10 is started to adjust the body of the clamp to a suitable position, then a standard test piece 23 is inserted into the corresponding clamp, and the fastening screw on the back plate 98 for the clamp is manually adjusted, such that the test piece is firmly fixed. A multi-channel controller of an upper monitor is used to control loading processes of respective modules to achieve a predetermined requirement for the test. During the test, a multi-channel data acquisition control card is used to transmit load data, displacement data acquired in each of the modules and image information sampled by the in-situ observation module to debugging software in the upper monitor. A constitutive relation of a material and a corresponding mathematical model about micro structure evolution are established through theoretical analysis, then parameters relating to material properties in the constitutive relation are determined through experiments, mathematical expressions of various common physical parameters are derived, and at the same time, a microstructure profile of the material is dynamically displayed on a corresponding imaging screen, then the entire in-situ testing based on multi-load and multi-physical field is accomplished.

The above is just a description of embodiments of the invention, and is not intended to limit the scope of the application. Various modifications and changes may be made by those skilled in the art. Any modifications, equivalents, and/or improvements made on the basis of the application shall fall within the scope of the application.

What is claimed is:

1. An in-situ testing equipment configured for testing micromechanical properties of a material in a multi-load and multi-physical field coupled condition, comprising a frame supporting module, a tension/compression-low cycle fatigue module, a torsioning module (21), a three-point bending module (6), an impressing module (33), a thermal field and magnetic field application module (34), an in-situ observation module (32) and a clamp body module (22), wherein:
the frame supporting module provides a structural support for the whole testing equipment;
the tension/compression-low cycle fatigue module is arranged at upper and lower ends of the testing equipment;
the torsioning module (21) is directly arranged at a front end of the tension/compression-low cycle fatigue module;
the three-point bending module (6), the impressing module (33) and the thermal field and magnetic field application module (34) are disposed on a support post at one side of the whole testing equipment through a common replacing component;
the in-situ observation module is disposed on another support post at the other side of the testing equipment;
the clamp body module is connected to a front segment of the torsioning module, so as to clamp a test piece;
an overall structure of the testing equipment is configured in a vertically symmetrical arrangement achieved by using four support posts;
two identical servo hydraulic cylinders (10) and two torsioning modules (21) are located at the upper and the lower ends of the testing equipment respectively and are used to perform a symmetrical tension/compression test and a symmetrical torsion test on the test piece (23) positioned centrally, to ensure that the geometrical center of the test piece (23) is maintained stationary during tension/compression and torsion tests, and to facilitate an in-situ dynamic observation on performances including deformation and damage of the material during the test;
the testing equipment is capable of realizing applications of five different types of loads including tension/compression, low cycle fatigue, torsion, bending and impressing, to perform an intensive study on micromechanical properties of the material in the multi-load and multi-physical field coupled condition by using built-in electric, thermal and magnetic application modules and the in-situ observation module, and to acquire relations between deformation behavior, mechanism of damage, performance weakening of the material, applied loads and material properties;
the tension/compression-low cycle fatigue module comprises the servo hydraulic cylinders (10) and a hydraulic cylinder fixing sleeve (13); by means of a mounting flange, the servo hydraulic cylinder (10) and the hydraulic cylinder fixing sleeve (13) mate with each other with a tolerance between an axle of the servo hydraulic cylinder and a hole of the hydraulic cylinder fixing sleeve, so as to ensure mounting accuracy, and are fastened by a second screw (11) and a second resilient washer (12); the hydraulic cylinder fixing sleeve (13) is rigidly fixed to the upper and lower support plates (7, 103) through a third screw (14) and a third resilient washer (15); the tension/compression-low cycle fatigue module utilizes two high-accuracy hydraulic cylinders (10) as a power source and accurately controls a displacement in the tension/compression low cycle fatigue process through controlling an amount of oil flowing into the servo hydraulic cylinders (10) and flow direction of the oil through a multi-channel servo controller; and
the torsioning module (21) comprises a torsion servo motor (44), a worm gear reducer and a ball spline (47); an output shaft of the torsion servo motor (44) is connected with a worm shaft (40) through a first key (42); a worm (41) and the worm shaft (40) are connected with each other through a key; a second sleeve (43) is used to maintain an axial position of an outer ring of a rolling bearing; the worm shaft (40) is supported within a mounting hole of a worm housing (35) through a first rolling bearing (38); an outer spline housing of the ball spline (47) is supported within the mounting hole of the worm housing (35) through a second sleeve (49) and a second rolling bearing (46); a worm wheel (50) is connected to the outer spline housing of the ball spline (47) through a second key (52); one end of the ball spline (47) is connected with a rod of the servo hydraulic cylinder (10) through a coupling sleeve (8) and an expansion sleeve (9), and the other end thereof is connected to the clamp body module (22) through an expansion sleeve; the torsioning module (21) utilizes the servo motor as a power source, and a torsion angle is output to a ball spline shaft connected with the rod of the hydraulic cylinder after reduction in speed via a worm gear having a large one-stage reduction gear ratio, so as to drive the rod and the clamp body module located at a front end to rotate as a whole.

2. The in-situ testing equipment according to claim 1, wherein the three-point bending module (6) comprises a bending servo motor (54), a transmission assembly comprising a ball screw (60) and a lead screw nut (61), a pressing head (64), and first and second guide rail-slider assemblies (71, 72); the bending servo motor (54) is fixedly connected to a motor flange (57) by a one-stage reducer (55); power is transmitted to the ball screw (60) via a coupling (58) from an output shaft of the reducer (55) and converted by the lead screw nut (61) into a linear movement of the pressing head (64) for bending; the first guide rail-slider assembly (71) is connected with a bending bottom plate (70), such that the three-point bending module (6) floats as a whole relative to a support plate (74) for the bending bottom plate, so as to achieve an internal force type bending; a nut coupling member (62) is guided by the second guide rail-slider assembly (72) to ensure linearity of displacement of the pressing head;

the impressing module (33) comprises an impression servo motor (75), a leading screw-nut assembly (89), piezoelectric ceramic (93), a flexible hinge (81), a force sensor (84), a capacitive displacement sensor (83) and a diamond impressing head (87); the impression servo motor (75) is mounted on a first bottom plate (77) through a flange (76); a second bottom plate (78) is mounted on the first bottom plate (77) through a LM guide rail-slider (96) for direction guidance; a support (79) for the displacement sensor is mounted via a manual translation platform (95) on a support (80) for the manual translation platform; the support (80) for the manual translation platform is fixed to the second bottom plate (78); the manual translation platform (95) is used to adjust an initial distance between a probe of the capacitive displacement sensor (83) and a reflective plate (85), and the probe of the displacement sensor is fixedly clamped by an adjusting screw (82); the capacitive displacement sensor (83) is placed within a recess located at a front end of the support (79) for the displacement sensor; the adjusting screw (82) is used to fixedly clamp the capacitive displacement sensor (83); the second bottom plate (78) is fixedly connected with the manual translation platform (95); the diamond impressing head (87) is mounted at one end of the force sensor (84) through a sleeve (86) for the impressing head, the other end of the force sensor is connected to the flexible hinge (81) through an external mounting bolt; a fastening screw (92) is used to fix the diamond impressing head (87); the piezoelectric ceramic (93) is mounted within a recess of the flexible hinge (81) and pre-fastened by a pre-pressing pad (94); the flexible hinge (81) is connected with the second bottom plate (78); power output from the impression servo motor (75) is converted into a linear movement through a leading screw-nut assembly (89) and transmitted b a seat (90) for the leading screw-nut to the flexible hinge (81) so as to be used as a coarse adjusting displacement during impressing; an actual impressing displacement is output by the piezoelectric ceramic; the leading screw-nut assembly (89) is fixed at both ends thereof by a second EK support (88) and an EF support base (91); the whole impressing module is mounted on a stationary support plate (5) used as a common mounting and replacing component through the support plate (74) for the bending bottom plate; and the clamp body module (22) comprises a clamp (97), a back plate (98) for the clamp, a body (99) of the clamp, a tension-torsion force sensor (100), a connecting body (101) and a lower connection-expansion sleeve (102); the lower connection-expansion sleeve (102) is connected with an output shaft of the torsioning module, and a tension force is provided through adjusting a screw on the back plate (98) for the clamp when the test piece is fixedly clamped.

3. The in-situ testing equipment according to claim 1, wherein the in-situ observation module is disposed on the frame supporting module;

the in-situ observation module comprises an instrument for testing and representing material properties;

the instrument comprises a 3D micro-imaging assembly having a large depth of field and an ultrasonic inspection device, and is capable of dynamically monitoring deformation and damage mechanism of the material, microstructural changes and transition of properties during the entire test in the complex mechanical loads and multi-physical field coupled condition.

4. The in-situ testing equipment according to claim 1, wherein the three-point bending module (6), the impressing module (33), the thermal field and magnetic field application module (34) are interchangeably arranged through a stationary support plate (5) used as a common mounting and replacing component, such that space required for arranging the modules are saved, and range of test can be enlarged as much as possible, while ensuring application of the coupled multi-load and multi-physical field; and the impressing module (33) is integrated on the frame supporting module through the stationary support plate (5) used as the common mounting and replacing component, such that an impressing test may be performed on the test piece in various states in which stress fields and physical fields are coupled in different ways.

5. The in-situ testing equipment according to claim 1, wherein the torsioning module (21) separates a tensioning/compressing movement in an axial direction from a torsioning movement by using a worm gear reducing mechanism and a cooperative ball spline; such that the tension/compression-low cycle fatigue module and the torsioning module (21) are independent from each other and do not interfere with each other.

6. The in-situ testing equipment according to claim 1, wherein in the three-point bending module (6), a first guide rail-slider assembly (71) is mounted under the bended bottom plate (70), such that the three-point bending module above can float above a support plate (74) for the bending bottom plate, and thereby an internal force type three-point bending is realized.

7. The in-situ testing equipment according to claim 1, wherein two opposite supporting heads (65) of the three-point bending module (6) are fixedly connected to a rear seat (66) for the supporting heads and are mounted within sliding beatings (68) through tail rotating shafts (67) located at ends of the supporting heads, so as to ensure that orientations of the two rear supporting heads (65) can adaptively adjusted, and a problem that the test piece (23) cannot contact the two supporting heads (65) simultaneously caused by misalignment during assembling and clamping can be eliminated.

8. The in-situ testing equipment according to claim 1, wherein the impressing module (33) is configured for adjusting an initial distance between a probe of a capacitive displacement sensor (83) and a reflective plate (85) through a manual translation platform (95).

9. The in-situ testing equipment according to claim 1, wherein the clamp body module (22) comprises an expansion sleeve for mounting and clamping the test piece.

10. The in-situ testing equipment according to claim 1, wherein the thermal field and magnetic field application module (34) comprises a permanent magnet (104) for providing a magnetic field; different intensities of the magnetic field are achieved by adjusting a relative position of a magnetic loop formed by the permanent magnet (104) and a soft iron (106) via an adjusting screw (105).

11. The in-situ testing equipment according to claim 1, wherein the thermal field and magnetic field application module (34) comprises a semiconductive Peltier sheet (107) for cooling the test piece, the Peltier sheet (107) is energized with a direct current in a given direction, and a large amount of heat is absorbed at a cooling side of the Peltier sheet due to Peltier effect, such that the temperature of the test piece is lowered so as to realize a cooling effect.

12. The in-situ testing equipment according to claim 1, wherein the test piece is heated by the thermal field and magnetic field application module (34) through light radiation; two symmetrical light-emitting bodies (108) are used to emit infrared light, and the light is reflected by two arc-shaped reflective surfaces and focused onto one point at the center of the test piece; a circulation water cooling system (109) is provided in the thermal field and magnetic field application module (34) to ensure that the temperature field inside the thermal field and magnetic field application module (34) will not be influenced by external temperature.

* * * * *